United States Patent [19]

Wohlrab et al.

[11] Patent Number: 5,476,843
[45] Date of Patent: Dec. 19, 1995

[54] STABLE TOPICAL FORMULATIONS WITH GOOD ACTIVE INGREDIENT RELEASE CHARACTERISTICS, CONTAINING AT LEAST ONE LIPOPHILIZED MACROLIDE ANTIBIOTIC

[75] Inventors: Wolfgang A. Wohlrab; Reinhard Neubert; Sabine Matschiner; Katrin Wellner, all of Halle, Germany

[73] Assignee: Roehm Pharma GmbH, Weiterstadt, Germany

[21] Appl. No.: 130,911

[22] Filed: Oct. 4, 1993

[30] Foreign Application Priority Data

Oct. 10, 1992 [DE] Germany .......................... 42 34 225.2

[51] Int. Cl.$^6$ .......................... C07H 17/08; A61K 31/70
[52] U.S. Cl. .................. 514/29; 514/28; 514/30; 514/291; 536/7.1; 536/7.2; 536/7.4
[58] Field of Search .................. 514/29, 28, 30, 514/291; 536/7.1, 7.2, 7.4

[56] References Cited

U.S. PATENT DOCUMENTS

| | | | |
|---|---|---|---|
| 3,891,755 | 6/1975 | Mehta | 514/29 |
| 3,922,379 | 11/1975 | Farhadieh | 424/441 |
| 3,934,013 | 1/1976 | Poulsen | 514/170 |
| 4,091,090 | 5/1978 | Sipos | 424/45 |
| 4,474,748 | 10/1984 | Sipos | 514/29 |

FOREIGN PATENT DOCUMENTS

| | | |
|---|---|---|
| 0043738 | 1/1982 | European Pat. Off. . |
| 0211258 | 2/1987 | European Pat. Off. . |
| 0211250 | 2/1987 | European Pat. Off. . |
| 0426029 | 5/1991 | European Pat. Off. . |
| 1944906 | 3/1970 | Germany . |
| WO90/08537 | 8/1990 | WIPO . |

*Primary Examiner*—Herbert J. Lilling
*Attorney, Agent, or Firm*—Oblon, Spivak, McClelland, Maier, & Neustadt

[57] ABSTRACT

A stable topical formulation with good active ingredient release characteristics, comprising at least one macrolide antibiotic which is lipophilized with at least one former of oppositely charged ions which is selected from the group consisting of alkyl sulfates, alkylsulfonates, and alkyl salicylates, RX, where R represents a linear and/or branched alkyl group with 6–32 C atoms, and X represents a sulfate, sulfonate, or salicylate group.

5 Claims, No Drawings

STABLE TOPICAL FORMULATIONS WITH GOOD ACTIVE INGREDIENT RELEASE CHARACTERISTICS, CONTAINING AT LEAST ONE LIPOPHILIZED MACROLIDE ANTIBIOTIC

BACKGROUND OF THE INVENTION

1. Field of the Invention

The invention relates to stable topical formulations with good active ingredient release characteristics, containing at least one macrolide antibiotic which is stabilized with at least one former of oppositely charged ions which has one or more linear and/or branched alkyl substituents.

2. Discussion of the Background

Macrolide antibiotics such as erythromycin belong to the group of drugs which are not well absorbed, because of their hydrophilic structural elements (Langguth, P. and Mutschler, E., 1987, Arzneim.-Forsch., 37 II, 12:1362–1366).

Bojarska-Dahlig, H., et al. (1981, "Curr. Chemother. Immunother. Proc. Int. Congr. Chemother.", 12th Meeting, Ed. Periti, P., and Gialdroni-Grassi, G., Am. Soc. Microbiol., Wash. D.C., Vol. 2. pp. 898–900) describe the lipophilization of erythromycin and erythromycin derivatives with 1,3-dioxolan-2-one units, and the resulting increase in antibacterial potency of erythromycin derivatives. The effect of newly introduced substituents on the stiffness and surface characteristics of the erythromycin molecule, and the influence of these parameters on the formation of ribosomal complexes in microorganisms, are discussed.

Eur. Pat. 0,426,029 (U.S. Ser. No. 89/428,803) describes a method of reduction of the lipophilicity of erythromycin and 6-0-methyl-erythromycin by incorporation of, e.q., substances in micelles which are comprised of steroids such as cholates, desoxycholates, glycocholates, etc. The result is injectable emulsions by means of which macrolide antibiotics may be administered intravenously.

In Jap. Pat. App. 62-029,511 (Eur. OS 211,250), lipophilic emulsions of erythromycin bases in an aqueous solution of a phosphatide are described which are produced under pressure by addition of additional emulsifiers. The lipophilic particles in the aqueous matrix have a mean diameter c. 0.1 micron.

PCT OS 90/08,537 describes formulations for oral administration of pharmaceutical compounds which comprise a therapeutically effective amount of a drug, further an organic solvent, an oil, and, optionally, lipophilic oppositely charged ions, stabilizers, and emulsifiers. The formulations contain, among other things, poorly absorbable antibiotics such as erythromycin, doxorubicin, gentamycin, or tosufloxacin. The oral availability of the erythromycin base is twice that provided by the customary tablet formulations.

Eur. Pat. 43,738 (=U.S. Pat. No. 4,954,487) relates to formulations for topical administration of pharmaceutical compounds which formulations comprise a medium for the transport of the drug through the intact skin, which medium is comprised of:

(1) Diols with 3–4 C atoms, diol esters, or diol ethers; and
(2) Cell wall perturbing substances such as alkenols, alkenylcarboxylic acids, fatty acids, and glycerides.

A formulation for topical application containing erythromycin showed improved skin penetration, and thereby proved effective as a drug for combating acne and other systemic disorders.

Currently commercially available preparations for topical application of macrolide antibiotics, particularly erythromycin preparations, have low release and stability of the active ingredient, and have high concentrations of volatile alcohols, e.g. ethanol or 2-propanol, whereby the volatility results in changes in the effectiveness and consistency of the preparation.

The publications of the state of the art concern

Reduction of the lipophilicity of macrolide antibiotics (Eur. OS 0,426,029); or

Increase of the lipophilicity, as is desired for topical application.

The method of lipophilization of erythromycin or its derivatives described by Bojarska-Dahlig et al., loc.cit., is expensive, starting with the expensive synthesis employed and therebeyond, and is intended for oral administration with high blood absorptivity and high resistance of the antibiotic to gastric juice.

The lipophilic emulsions claimed in Jap. Pat. App. 62/029,511 are administered parenterally and thus are unsuitable for topical application, as are the oral formulations in gelatin capsules claimed in PCT OS 90/08537, which contain oil, organic solvents, and other additives in addition to the active principle (erythromycin).

The formulations for topical administration of drugs which formulations are described in Eur. Pat. 43,738 contain, e.q., erythromycin as the active ingredient, and diols or diol derivatives, and alkenols and alkenol derivatives, as additives. These costly formulations contain a certain proportion of volatile substances which lead to the above-described problems concerning stability over time.

Accordingly, a need continues to exist for lipophilized macrolide antibiotics, and/or formulations containing macrolide antibiotics, for topical administration which exhibit good active principle release characteristics.

SUMMARY OF THE INVENTION

Accordingly, one object of the present invention is to provide a macrolide antibiotic formulation of improved antibacterial activity, particularly against gram-positive activity.

Briefly, the object and other objects of the present invention as hereinafter will become more readily apparent can be attained by a stable topical formulation of improved active ingredient release characteristics which comprises at least one macrolide antibiotic which is lipophilized with at least one former of oppositely charged ions, wherein the ions are selected from the group consisting of alkyl sulfates, alkyl sulfonates, and alkyl salicylates, RX, wherein R is a linear and/or branched alkyl group of 6–32 carbon atoms and X is a sulfate, sulfonate or salicylate group.

DETAILED DESCRIPTION OF THE PREFERRED EMBODIMENTS

The formulation of the present invention provides excellent stability and release characteristics in salve preparations for topical application. The saturation solubilities of the inventive combinations comprised of a macrolide antibiotic and an oppositely charged ion, in dermatologically useful vehicles such as propylene glycol, are much higher than the saturation solubility of the unmodified macrolide antibiotic.

The-macrolide-antibiotics:

Macrolide antibiotics have excellent antibacterial activity, particularly against gram-positive bacteria The macrolide antibiotics are classified according to the size of the macrocyclic lactone ring. Macrolide antibiotics are polyfunctional molecules, most of which have at least one amine sugar and are basic (see Kirk-Othmer, 1978, "Encyclopedia of Chemical Technology", 3rd Ed Vol 2. pub. J. Wiley, p. 937). They are produced as secondary metabolites of microorganisms which preferably are found in the soil, particularly various strains of Streptomyces. Commercially, macrolide antibiotics are produced as complex mixtures of related compounds, by the aerobic submersed fermentation of suitable cultures at 20°–40° C. The desired compounds are separated out, following adjustment of the pH of the fermentation solution to 9.5, by extraction with suitable solvents, eg ethyl acetate, chloroform, or methylene chloride, followed by precipitation of the raw crystalline product, and refinement by chromatography (Kirk-Othmer, loc..cit., p. 940).

Suitable macrolide antibiotics include those with 12-member lactone rings such as methymycin (the first macrolide to have its structure elucidated) and neomethymycin. Also included are macrolide antibiotics. with 14-member lactone rings, of which the preferred representatives are the erythromycins, produced from *Streptomyces erythreus*. Examples include: erythromycin A, erythromycin B, erythromycin C, erythromycin D, erythromycin E, erythromycin estolate, erythronolid, and clarythromycin. Other examples of macrolide antibiotics with 14-member lactone rings include: megalomycin and its derivatives, picromycin, narbomycin, oleandomycin, triacetyl-oleandomycin; and the neutral compounds laukamycin, kujimycin A. albocyclin, and cineromycin B.

Macrolide antibiotics having 16-member rings are suitable and include carbomycin (Magnamycin) and its derivatives (e.g. niddamycin), spiramycin and its derivatives, leucomycin and its derivatives (e.g. midecamycin, maridomycin, tylosin, cirramycin, and juvenimicins); and the neutral representatives chalcomycin and neutramycin loc.cit., pp. 941–950).

Examples of macrolide antibiotics with larger lactone rings, e.g. having 26–40 or more ring members, include pimaricin, lucensomycin, nystatin, amphotericin B, hamycin, candicidin A and B, candidin, and levorin. The effectiveness of this group is practically exclusively against fungi and yeasts. Bacteria are not affected or only slightly affected, wherewith the toxicity of these substances is low in every case (see 1980, "Ullmanns Enzyklopaedie der technischen Chemie", 4th Ed., Vol. 9, pub. Verlag Chemie, of Weinheim, pp. 673 and 674).

Clinically, macrolide antibiotics are used principally for treating infections with Streptococci, Staphylococci, and Pneumococci. Generally the toxicity of macrolide antibiotics is low. Esters of macrolide antibiotics have become therapeutically important because, when administered orally, they result rapidly in higher blood levels, and further they are practically free of odor and taste and are highly stable.

The lipophilizing formers of oppositely charged ions:

In PCT OS 90/08537, "lipophilic oppositely charged ions" are described which are formed by organic acids or their salts, and which have pKa values which are sufficiently small that dissociation at pH values prevalent in the formulations is assured. The organic acids comprise oleic acid, alkylsulfonic acids, salicylic acid, bile acids (acids of specific steroids), palmitic acid, and other aliphatic acids. Suitable formers of oppositely charged ions of the present invention include alkyl sulfates, alkylsulfonates, and alkyl salicylates, RX, where R represents a branched or linear alkyl group with 6–32 C atoms, and X represents a sulfate, sulfonate, or salicylate group.

Preferred are alkyl groups R with 12–32 C atoms, particularly 16–24 C atoms. Preferred groups X are the sulfate and sulfonate groups.

Examples of formers of oppositely charged ions which are suitable include hexyl salicylate, heptyl salicylate, octyl salicylate, isooctyl salicylate, nonyl salicylate, decyl salicylate, isodecyl salicyate, undecyl salicylate, dodecyl salicylate, tetradecyl salicylate, isotetradecyl salicylate, hexadecyl salicylate, octadecyl salicylate, eicosyl salicylate, hexyl sulfate, octyl sulfate, isooctyl sulfate, decyl sulfate, isodecyl sulfate, dodecyl sulfate, tetradecyl sulfate, isotetradecyl sulfate, hexadecyl sulfate, octadecyl sulfate, eicosyl sulfate, hexylsulfonate, octylsulfonate, isooctylsulfonate, decylsulfonate, isodecylsulfonate, dodecylsulfonate, tetradecylsulfonate, isotetradecylsulfonate, hexadecylsulfonate, octadecylsulfonate, and eicosylsulfonate.

The partition equilibrium in the system n-octanol/aqueous phosphate buffer can serve as an indication of the particular effect of a given former of oppositely charged ions on the lipophilization of macrolide antibiotics. This equilibrium is characterized by the partition coefficient P, which is the quotient of the concentration of the macrolide antibiotic in the n-octanol (numerator) and the concentration of the macrolide antibiotic in the aqueous phosphate buffer (denominator). The value of P is a measure of the liphophilicity of the combination of the macrolide antibiotic and the former of oppositely charged ions. The partition equilibrium of erythromycin base in the system n-octanol/aqueous phosphate buffer is studied for various formers of oppositely charged ions, over a physiologically relevant pH range, viz. between pH 6.0 (absorbent skin surface) and pH 7.4 (mean pH of blood).

Table 1 shows that among the formers of oppositely charged ions tested, dodecyl sulfate and octadecylsulfonate are suitable for providing a partition equilibrium with a high proportion of the erythromycin+oppositely charged ion being in the lipophilic phase, and this effect is largely independent of pH. Comparison with formers of oppositely charged ions according to the state of the art, e.g. deoxycholate, dehydrocholate, octanoic acid, dodecanoic acid, or cyclamate, shows the superiority of the inventive formers of oppositely charged ions in the lipophilization of erythromycin base. The partition coefficients P are appreciably higher and are quite independent of the pH of the aqueous phase.

The dicarboxylic acid, azelaic acid, was studied because of its benefits as a therapeutic agent for acne. It is unsuitable as a lipophilizing former of oppositely charged ions, however, particularly at low pH values. A consideration of the partition coefficients P for erythromycin as a function of the concentration of the former of oppositely charged ions at constant pH=7.4 shows that, in addition to the advantageously functioning dodecyl sulfate and octadecylsulfonate of the present invention, hexyl salicylate also has a good lipophilizing effect at ratios of erythromycin to hexyl salicylate of 1:2 or less (Table 2) (cf. the pH-dependent study, where the advantage of hexyl salicylate was only slight).

Release studies on semisolid preparations containing lipophilized erythromycin:

Semisolid preparations, e.g. cremes, salves, or pastes, are the preferred formulations of topical macrolide antibiotics. Suitable bases for cremes include waxlike substances which are melted, followed by addition of the active principle, and cooling with stirring. In general the formulation process is then continued in a roll mill, to provide a specified particle size of the dispersed active principle. Pastes are produced similarly, but with higher solids content.

Cremes comprise semisolid water/oil or oil/water emulsions. In general, the components of both phases are heated separately to 70°–80° C., and then are mixed together by stirring, with cooling, to form the emulsion. To further comminute the emulsified droplets, the emulsion may be processed on a homogenizing apparatus, e.g. a colloid mill, prior to final cooling (see, e.q., Kirk-Othmer, 1982, loc.cit., Vol. 17, p. 285).

The preferred form for semisolid preparations of the present lipophilized macrolide antibiotics is a stable salve. Toward this end, one preliminarily determines the saturation solubilities in the vehicles being considered for the dermatological application; these solubilities are important parameters. The decomposition of erythromycin in aqueous media is a factor here; it necessitates exclusion of water as a component of the vehicle. Another factor when acne is to be treated is the desire to avoid fatty vehicles to the extent possible. Numerous solvents which are studied include paraffins, Miglyol (a mixture of glycerides), octanoic acid, isopropyl myristate, palmitic acid isopropyl ester, ethylene glycol, hexadecane, polyethylene glycol 400, and the like, and propylene glycol, glycerin, and hexylene glycol are particularly effective for providing stable salve preparations. Table 3 infra gives the saturation solubilities of erythromycin alone and its opposite-ion complexes erythromycin octylsulfonate and erythromycin hexyl salicylate, in the solvents glycerin and propylene glycol, which solvents are taken as examples of vehicles which may be useful for dermatologic applications. In glycerin, only erythromycin octylsulfonate shows higher solubility than erythromycin alone, while in propylene glycol both of the erythromycin opposite-ion complexes considered here are more soluble than erythromycin alone; and the solubilities of erythromycin and the complexes in propylene glycol are distinctly better than in glycerin. Erythromycin octadecylsulfonate has excellent saturation solubility in hexylene glycol.

The release studies are carried out using a multiple membrane model (Neubert, R., and Wohlrab, W., 1990 *Acta Pharm. Technol.*, 36, 4:197–200), with the analysis using the method of Dabrowska et al., 1984 *Sci.Pharm.*, 52, 220–228. Four membranes are employed. The first membrane is comprised of Nephrophan® saturated with dodecanol and phosphate buffer (pH=5.5) and dried. The three successively adjacent membranes are comprised of a mixture of 50 wt. % collodion and 50 wt. % dodecanol. After the salves are applied (topical preparations each containing 2% erythromycin) and are tempered at 32° C., during a period of 200 min, 0.2 ml 0.1N NaOH solution and 3 ml chloroform are added to each of the membranes, followed by shaking or the like for 30 min. The chloroform phase is separated and is shaken an additional 30 min with a mixture of 3 ml phosphate buffer (pH=5.3) and 3 ml aqueous bromocresol purple solution. (A 4 ml amount of 0.1NaOH solution was added to 0.1727 g bromocresol purple, distilled water was added to make up 200 ml, and the mixture was filtered.) Then the chloroform phase is shaken with 2 ml 0.1N NaOH and the aqueous phase is measured photometrically at 590 nm. The recovery of erythromycin from the dodecanol-collodion embranes is 96.2%.

In Table 4 infra the cumulative erythromycin contents of the membranes at various times are given. All formulations contain 2% erythromycin as active principle. The formulations of the table are the formulation according to the invention (with erythromycin octadecylsulfonate) and Zineryt® salve (supplied by the firm Roehm Pharma), as a comparison formulation. Zineryt® is used for acne therapy and contains 2% erythromycin as active principle. The formulations according to the invention have better topical availability as indicated by their accumulation in the four membranes.

A particularly effective salve formulation as to release characteristics is formulation III of Table 5, which contains propylene glycol, hexylene glycol, palmitic acid, and glycerin as the salve base.

ADVANTAGES OF THE INVENTION

The macrolide antibiotics lipophilized with the formers of oppositely charged ions of the present invention have excellent solubility in lipophilic media, wherewith under conditions of contact with aqueous media this solubility remains at a constant high level in the physiologically significant pH range 6.0–7.4. In contrast, with opposite ion complexes of the state of the art, there is observed a major decrease in the lipophilic character of the macrolide antibiotics when contacted with aqueous media.

In the form of semisolid preparations of the type preferred for topical applications, the present complexes of macrolide antibiotics and oppositely charged ions have release characteristics which are superior to those of ordinary commercial formulations.

The stability of the present complexes in aqueous preparations is appreciably higher than that of the pure macrolide antibiotics, particularly in the case of erythromycin.

TABLE 1

Partition coefficient P of erythromycin for various formers of oppositely charged ions (OIFs), and various values of pH of the aqueous phosphate buffer, in the system n-octanol/aqueous phosphate buffer:

| Former of Oppositely charged ions (molar ratio of OIF to erythromycin = 1:1) | P, at various values of pH | | |
|---|---|---|---|
|  | pH 6.0 | pH 6.8 | pH 7.4 |
| Octadecylsulfonate | 28.5 ± 2.1 | 29.1 ± 3.3 | 27.1 ± 2.5 |
| Dodecyl sulfate | 20.6 ± 1.7 | 21.7 ± 1.1 | 20.1 ± 0.7 |
| Hexyl salicylate | 6.2 ± 0.7 | 10.5 ± 0.3 | 10.5 ± 0.4 |
| Comparison Examples: | | | |
| Deoxycholate | 5.4 ± 0.7 | 9.2 ± 0.3 | 10.1 ± 0.5 |
| Dehydrocholate | 0.3 ± 0.1 | 4.5 ± 0.2 | 10.9 ± 0.2 |
| Octanoic acid | 4.9 ± 0.1 | 7.5 ± 1.1 | 15.1 ± 0.2 |
| Dodecanoic acid | <0.01 | 4.2 ± 0.8 | 5.9 ± 0.2 |
| Cyclamate | 4.2 ± 0.7 | 8.7 ± 0.6 | 9.7 ± 0.2 |
| Azelaic Acid | <0.01 | 4.2 ± 0.8 | 5.3 ± 0.3 |
| No opposite-ion former | 0.2 ± 0.2 | 2.9 ± 1.2 | 5.5 ± 0.4 |

TABLE 2

Partition coefficient P of erythromycin for various concentrations of formers of oppositely charged ions (OIFs), in the system n-octanol/aqueous phosphate buffer, at pH = 7.4:

| Opposite-ion former | Partition coefficient P, for molar ratio of erythromycin to OIF of | | |
|---|---|---|---|
|  | 1:1 | 1:2 | 1:5 |
| Octadecylsulfonate | 27.1 ± 2.5 | 30.1 ± 3.6 | 28.3 ± 2.5 |
| Dodecyl sulfate | 20.1 ± 0.7 | 23.8 ± 1.3 | 22.3 ± 1.4 |
| Hexyl salicylate | 10.5 ± 0.4 | 24.4 ± 3.2 | 21.0 ± 1.0 |
| Comparison Examples: | | | |
| Deoxycholate | 10.1 ± 0.5 | 9.6 ± 1.2 | 11.2 ± 0.9 |
| Dehydrocholate | 10.9 ± 0.2 | 14.8 ± 2.2 | 17.5 ± 1.6 |
| octanoic acid | 15.1 ± 2.0 | 12.9 ± 1.3 | 14.1 ± 0.6 |
| Dodecanoic acid | 5.9 ± 0.2 | 5.7 ± 0.1 | 6.3 ± 0.5 |
| Cyclamate | 9.7 ± 0.2 | 9.6 ± 0.8 | 9.5 ± 1.4 |
| Azelaic acid | 5.3 ± 0.2 | 5.4 ± 0.2 | 5.9 ± 0.3 |
| No opposite-ion former | 5.5 ± 0.4 | | |

TABLE 3

Saturation solubilities SL of erythromycin (E) and the lipophilized complexes erythromycin hexyl salicylate ($E^+HS^-$), erythromycin octylsulfonate ($E^+OS^-$), and erythromycin octadecylsulfonate ($E^+ODS^-$), in dermatologically useful vehicles:

| Vehicle | Saturation solubility SL (ma/mi): | | | |
|---|---|---|---|---|
|  | E | $E^+HS^-$ | $E^+OS^-$ | $E^+ODS^-$ |
| Glycerin | 1.9 | 1.6 | 3.4 | — |
| Propylene glycol | 6.7 | 12.2 | 20.8 | — |
| Hexylene glycol | — | — | — | >20 |

Note:
SL was determined according to known methods (e.q. 1990, "Roempps Chemielexikon", 9th Ed., Vol. 3, pub. Thieme-Verlag, Stuttgart, up. 2537–2540). The samples were tempered 3 hr at 32° C. with shaking every 10 min.

TABLE 4

Test of release characteristics of erythromycin active principle on a multilayer membrane model; comparison with a commercially available product:

| First membrane: | Nephrophan ® saturated with dodecanol, dried, and then saturated with aqueous phosphate buffer (pH 5.5) |
|---|---|
| Second to fourth membranes: | 50 wt. % collodium, 50 wt. % dodecanol. |

Content of erythromycin or erythromycin/opposite ion complex, as a percentage of the originally employed amount of erythromycin (%)

| Time (min) | Formulation | Membranes 1–4, tot. | Membranes 2–4, tot. |
|---|---|---|---|
| 15 | I | 19.9 | 8.6 |
|  | II | 20.3 | 9.0 |
|  | ZE | 7.3 | 1.4 |
| 30 | I | 33.2 | 17.3 |
|  | II | 28.8 | 15.0 |
|  | ZE | 10.4 | 1.9 |
| 60 | I | 53.4 | 32.4 |
|  | II | 49.1 | 30.6 |
|  | ZE | 20.8 | 9.8 |

KEY to Table 4:
I Salve base:   15 parts Macrogol (polyethylene glycol) stearate
                10 parts propylene glycol
                75 parts glycerin.
2.8% erythromycin octadecylsulfonate, corresponding to 2% erythromycin.
II Salve base:  15 parts Macrogol stearate
                10 parts propylene glycol
                72 parts glycerin
                3 parts zinc oxide.
2.8% erythromycin octadecylsulfonate, corresponding to 2% erythromycin.
ZE Zineryt ®, supplied by the firm Roehm Pharma, containing 2% erythromycin.

TABLE 5

Test of release characteristics of erythromycin active principle on a multilayer membrane model, with the aim of finding a particularly effective salve formulation:

| First membrane: | 84 wt. % collodion, 16 wt. % dodecanol, dried, and then saturated with phosphate buffer (pH 5.5). |
|---|---|
| Second to fourth membranes: | 50 wt. % collodion, 50 wt. % dodecanol. |

Content of erythromycin octadecylsulfonate, as a percentage of the originally employed amount of erythromycin

| Time (min) | Formulation | Membranes 1–4, tot. | Membranes 2–4 tot. |
|---|---|---|---|
| 15 | I | 25.0 | 8.8 |
|  | II | 21.6 | 7.9 |
|  | III | 34.6 | 10.8 |
|  | IV | 21.8 | 7.3 |
| 30 | I | 35.6 | 15.6 |
|  | II | 41.7 | 17.8 |
|  | III | 57.8 | 18.4 |
|  | IV | 36.7 | 11.0 |
| 60 | I | 52.0 | 16.4 |
|  | II | 60.5 | 20.6 |
|  | III | 69.9 | 23.1 |

TABLE 5-continued

| I | V | 62.4 | 26.6 |
|---|---|------|------|

KEY to Table 5:
I Salve base:  15 parts Macrogol (polyethylene glycol) stearate
               10 parts propylene glycol
               72 parts glycerin
               3 parts zinc oxide.
(Corresponds to II of Table 4.)
II Salve base: 15 parts Macrogol stearate
               10 parts propylene glycol
               75 parts glycerin.
(Corresponds to I of Table 4.)
III Salve base: 10 parts propylene glycol
                10 parts hexylene glycol
                5 parts palmitic acid
                75 parts glycerin.
IV Salve base: 15 parts cetyl alcohol and stearyl alcohol
               10 parts propylene glycol
               10 parts hexylene glycol
               65 parts glycerin.

All of the salve formulations II-IV contain 2.8% erythromycin octadecylsulfonate as the active principle, corresponding to 2% erythromycin (based on the overall formulation). Having now fully described the invention, it will be apparent to one of ordinary skill in the art that many changes and modifications can be made thereto without departing from the spirit or scope of the invention as set forth herein.

What is claimed as new and desired to be secured by Letters Patent of the United States is:

1. A stable topical formulation with good active ingredient release characteristics, which comprises a therapeutically effective amount of one or more 14-membered lactone ring macrolide antibiotics which are lipophilized with octadecyl sulfonate.

2. The stable topical formulation of claim 1, wherein said one or more 14-membered lactone ring macrolids antibiotics are selected from the group consisting of erythromycin A, erythromycin B, erythromycin C, erythromycin D, erythromycin E, erythromycin estolate, erythronolid, clathyromycin, megalomycin, picromycin, narbomycin, oleandomycin, triacetyl-oleandomycin, laukamycin, kujimycin A, albocyclin and cineromycin B.

3. The stable topical formulation of claim 1, which is a salve, which comprises one or more substances selected from the group consisting of propylene glycol, glycerin, hexylene glycol, cetyl alcohol/steryl alcohol, polyethylene glycol stearate and palmitic acid.

4. A stable topical formulation with good active ingredient release characteristics, which comprises a therapeutically effective amount of erythromycin which is lipophilized with octadecyl sulfonate.

5. The stable topical formulation of claim 2, which is a salve, which comprises one or more substances selected from the group consisting of propylene glycol, glycerin, hexylene glycol, cetyl alcohol/steryl alcohol, polyethylene glycol stearate and palmitic acid.

* * * * *

UNITED STATES PATENT AND TRADEMARK OFFICE
CERTIFICATE OF CORRECTION

PATENT NO. : 5,476,843
DATED : Dec. 19, 1995
INVENTOR(S) : Wolfgang A. WOHLRAB, et al.

It is certified that error appears in the above-indentified patent and that said Letters Patent is hereby corrected as shown below:

On the title page, in Item [75], the third inventor should read:

--Sybille MATSCHINER--

Signed and Sealed this

Thirtieth Day of July, 1996

Attest:

BRUCE LEHMAN

Attesting Officer    Commissioner of Patents and Trademarks